United States Patent [19]
Brady et al.

[11] Patent Number: 4,609,725
[45] Date of Patent: Sep. 2, 1986

[54] CARDIAC ATRIAL PEPTIDES

[75] Inventors: Stephen F. Brady, Philadelphia, Pa.; Mary A. Napier, Edison, N.J.; Ruth F. Nutt, Green Lane, Pa.; Richard L. Vandlen, Summit, N.J.

[73] Assignee: Merck & Co., Inc., Rahway, N.J.

[21] Appl. No.: 658,350

[22] Filed: Oct. 9, 1984

[51] Int. Cl.⁴ .................................................. C07K 7/12
[52] U.S. Cl. ..................................... 530/324; 530/325
[58] Field of Search .................................. 260/112.5 R

[56] References Cited
U.S. PATENT DOCUMENTS 4,448,764  5/1984  Smith et al. ............................ 424/1.1
4,460,559  7/1984  Goldenberg ............................ 424/1.1

OTHER PUBLICATIONS

Gutkowska et al., *Biochemical and Biophysical Research Communications*, 122(2), 593–601, Jul. 31, 1984.
Kangawa et al., *Biochemical and Biophysical Research Communications*, 118(1), 131–139, Jan. 13, 1984.
Seidah et al., *Proc. Natl. Acad. Sci.*, USA, 81, 2640–2644, May 1984.
Guttman, *Calcitonin*, 1980, Proceedings of an International Symposium held in Milan, Oct. 15–17, 1980.
Rittel et al., *Experientia*, 32(2), 246–248 (1976).

*Primary Examiner*—Delbert R. Phillips
*Attorney, Agent, or Firm*—Donald J. Perrella; Hesna J. Pfeiffer

[57] ABSTRACT

Monoiodinated-tyrosine derivatives of synthetic fragments of mammalian atrial natriuretic factor are biologically active and are useful to determine the mode of biological activity and the effect of derivatization on biological activity.

4 Claims, No Drawings

CARDIAC ATRIAL PEPTIDES

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalamic hormone important in regulating the osmotic concentration of the body fluids.

The postulated existence of a substance which would enhance urinary sodium excretion, and hence be involved in regulation of extracellular fluid volume, was demonstrated recently. De Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297–302, 1983) and atriopeptin (Currie et al., Science 111: 67, 1984). Atrial natriuretic factor was shown to be a family of peptides all of which have a common amino acid sequence but differ in length by the presence or absence of 1–8 amino acids on the amino or carboxyl termini.

Peptide chemists quickly produced completely synthetic material that mimicked the biological activity of the family of peptides that have been isolated from the cardiac atria.

The biological activity of ANF indicates utility in congestive heart failure where standard therapy utilizes potent diuretics in combination with peripheral vasodilating drugs. Atrial natriuretic factor combines both of these actions in one molecule which is produced naturally within the body. It is possible that the salt and water retention associated with congestive heart failure is a result of inadequate production of ANF. If such is true, administration of ANF would allow for replacement of adequate quantities of the material.

A second major disease for which the biological activity of ANF indicates utility is essential hypertension. Standard therapy for hypertension utilizes diuretic and peripheral vasodilating drugs. Atrial natriuretic factor incorporates both of these characteristics. A specific use also may be found in the acute treatment of hypertensive crisis such as malignant hypertension where the powerful vasodilating effect of ANF would be paramount.

In addition to these two very broad categories of therapeutic utility, it is possible that those diseases which are characterized by decreases in renal function may benefit because of the favorable action of ANF on renal hemodynamics, especially enhancement of medullary blood flow.

OBJECTS OF THE INVENTION

It is an object of the present invention to provide monoiodinated derivatives of a synthetic fragment of rat atrial natriuretic factor (ANF). Another object is to provide monoiodinated derivatives of a synthetic fragment of rat ANF which has the biological activity of mammalian atrial natriuretic factor. Still another object is to provide a monoiodinated derivative of a synthetic fragment of ANF which is useful as a reference standard in producing the non-iodinated synthetic fragment of ANF. A further object is to provide a compound which enables the metabolic half-life of ANF to be followed in clinical and in vitro studies. Yet another object is to provide a method for synthesizing the monoiodinated derivative. These and other objects of the present invention will be apparent from the following description.

SUMMARY OF THE INVENTION

Monoiodinated-tyrosine derivatives of synthetic fragment of rat atrial natriuretic factor which may be produced by iodination of the corresponding synthetic fragment are biologically active and are useful to determine the mode of biological activity and the effect of derivatization on biological activity.

DETAILED DESCRIPTION

One embodiment of the monoiodinated tyrosine derivatives of ANF of the present invention has the formula Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-(I-Tyr). This non-iodinated fragment is a known peptide which has been isolated, sequenced and synthesized as disclosed by Seidah et al., Proc. Natl. Acad. Sci. 81: 2640–2644, 1984. Other fragments may be obtained by extending or reducing the amino acid sequence at its N-terminal end or at its C-terminal end in accordance with procedures known to skilled peptide chemists. In addition, replacement of the Ile residue in the 10 position by methionine (Met), again by employment of known techniques, gives fragments having an amino acid sequence corresponding to the corresponding portion of human ANF. Specific peptides that fall within the scope of the present invention are the following: A-Cys-Phe-Gly-Gly-Arg-X-Asp-Arg-Ile-Gly-Ala-Gln-Ser-Gly-Leu-Gly-Cys-Asn-Ser-Phe-Arg-(I-Tyr)-B wherein X is Ile or Met, wherein A is Ser—

-continued

```
                                            Ser—Ser—
                                       Arg—Ser—Ser—
                                  Arg—Arg—Ser—Ser—
                              Leu—Arg—Arg—Ser—Ser—
                          Ser—Leu—Arg—Arg—Ser—Ser—
                      Arg—Ser—Leu—Arg—Arg—Ser—Ser—
                  Pro—Arg—Ser—Leu—Arg—Arg—Ser—Ser—
              Gly—Pro—Arg—Ser—Leu—Arg—Arg—Ser—Ser—
          Ala—Gly—Pro—Arg—Ser—Leu—Arg—Arg—Ser—Ser—
      Leu—Ala—Gly—Pro—Arg—Ser—Leu—Arg—Arg—Ser—Ser—
``` and wherein B is —Arg or —Arg—Arg. These peptides may be linear or cyclized by means of covalent, e.g., disulfide, bonds between the two cysteine residues. The monoiodinated derivative is prepared by treating the noniodinated peptide, in a medium containing sodium phosphate buffer, sodium iodide, with chloramine-T (N-chloro-4-methylbenzenesulfonamide sodium salt). The iodination is quenched by addition of sodium thiosulfate and the iodinated peptide isolated by a high performance liquid chromatography (HPLC) column. The radioactively iodinated peptide is prepared similarly using $I^{125}$.

The iodinated derivative is useful as a reference standard in synthesis of the noniodinated synthetic peptides while the radioactively iodinated peptide is useful in in vitro and clinical metabolic half-life studies of ANF. The iodinated derivative has substantially the same biological activity as the non-iodinated peptide.

The following example illustrates the present invention without, however, limiting the same thereto.

EXAMPLE

The monoiodo-tyrosine derivative of an ANF peptide fragment was prepared by a modification of the method of Hunter and Greenwood, Nature 194: 670–677 (1962), using chloramine-T. The 26-amino acid synthetic ANF described by Seidah et al., supra., 100 μg (31 nmoles) in 50 μl distilled $H_2O$, was combined with 100 μl 0.5M sodium phosphate, pH 7.6, and NaI (15 nmoles) in 2.2 μl buffer containing a tracer amount of Na [$^{125}$I] (Amersham). Iodination was initiated by addition of 15 μl chloramine-T solution (2 mg/ml in 0.05M Na phosphate, pH 7.6). After 30 seconds, the reaction was quenched by addition of 20 μl Na thiosulfate (3 mg/ml in 0.05M Na phosphate buffer) and the reaction mixture was immediately injected onto the C18 reverse phase HPLC column equilibrated with aqueous 0.1% trifluoroacetic acid. Elution was achieved by a linear gradient of acetonitrile (0 to 50%) over 40 minutes at a flow rate of 1 ml/minute. One minute fractions were collected. The HPLC fractions containing the iodinated and non-iodinated ANF peptide fragments were lyophilized, and the peptide content quantitated by SPINCO amino acid analysis.

The monoiodinated synthetic ANF peptide fragment eluted from the reverse phase HPLC column well separated (ca. 2 min) from the unlabeled and di-iodo forms of the ANF peptide fragment. Using a low ratio of iodide to peptide during the radioiodination procedure, only a single iodinated product was obtained. The antigenicity of the $^{125}$I-ANF peptide fragment was retained as shown by immunoprecipitation with rabbit anti-ANF antibodies and by binding of 70 to 90% of the radioactivity to an anti-ANF IgG affinity column. Enzymatic treatment of the $^{125}$I-ANF peptide fragment sample with carboxypeptidase A, previously shown to remove only the C-terminal tyrosine from ANF peptide fragment, and subsequent HPLC chromatography of the reaction products, resulted in the removal of 90% of the $^{125}$I from the original peptide. Co-chromatography with cold mono-iodo- and di-iodo-tyrosine indicated that the radiolabeled product was the mono-iodo($^{125}$I)-tyrosine ANF peptide fragment.

Under the conditions described above, conversion of non-iodinated ANF peptide fragment to the iodinated peptide was approximately 48%, based on the absorbance of the respective HPLC fractions and by amino acid analysis. The iodinated ANF peptide fragment gave complete vasorelaxation of serotonin contracted rabbit ($IC_{50}=1650$ pM) and rat ($IC_{50}=1050$ pM) aortae but required a slightly higher concentration than the non-iodinated ANF peptide fragment (550 pM and 850 pM, respectively) for 50% relaxation.

What is claimed is:

1. A peptide comprising one of the amino acid sequences: A-Cys-Phe-Gly-Gly-Arg-X-Asp-Arg-Ile-Gly-Ala-Gln-Ser-Gly-Leu-Gly-Cys-Asn-Ser-Phe-Arg-(I-Tyr)-B wherein X is Ile or Met, A is absent or present and if present is:

```
                                            Ser—
                                       Ser—Ser—
                                  Arg—Ser—Ser—
                              Arg—Arg—Ser—Ser—
                          Leu—Arg—Arg—Ser—Ser—
                      Ser—Leu—Arg—Arg—Ser—Ser—
                  Arg—Ser—Leu—Arg—Arg—Ser—Ser—
              Pro—Arg—Ser—Leu—Arg—Arg—Ser—Ser—
          Gly—Pro—Arg—Ser—Leu—Arg—Arg—Ser—Ser—
      Ala—Gly—Pro—Arg—Ser—Leu—Arg—Arg—Ser—Ser—
  Leu—Ala—Gly—Pro—Arg—Ser—Leu—Arg—Arg—Ser—Ser—
``` and B is absent or present and if present is -Arg or -Arg-Arg, and wherein the I atom is nonradioactive or radioactive and the peptide is linear or cyclized by means of covalent bonds between the two cysteine residues.

2. A peptide of claim 1 wherein X is Ile.

3. A peptide of claim 1 wherein X is Met.

4. A peptide of claim 1 wherein X is Ile, A is Arg-Arg-Ser-Ser and B is absent.

* * * * *